US009023261B2

(12) United States Patent
Mullane

(10) Patent No.: US 9,023,261 B2
(45) Date of Patent: *May 5, 2015

(54) METHOD AND APPARATUS FOR MAKING AN APERTURED WEB

(75) Inventor: Timothy Ian Mullane, Union, KY (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 13/568,180

(22) Filed: Aug. 7, 2012

(65) Prior Publication Data
US 2012/0295060 A1 Nov. 22, 2012

Related U.S. Application Data

(63) Continuation of application No. 11/249,618, filed on Oct. 13, 2005, now Pat. No. 8,241,543, which is a continuation-in-part of application No. 10/913,199, filed on Aug. 6, 2004, now abandoned.

(60) Provisional application No. 60/493,207, filed on Aug. 7, 2003.

(51) Int. Cl.
B29C 59/04 (2006.01)
B26F 1/18 (2006.01)
(Continued)

(52) U.S. Cl.
CPC ... *B26F 1/18* (2013.01); *B26F 1/20* (2013.01); *B26F 1/24* (2013.01); *B29C 55/18* (2013.01); *B29C 59/022* (2013.01); *B29C 59/04* (2013.01); *B29K 2105/256* (2013.01)

(58) Field of Classification Search
USPC .......... 264/154, 155, 156, 273; 425/294, 362, 425/290, 385, 404; 156/252, 253
See application file for complete search history.

(56) References Cited

U.S. PATENT DOCUMENTS 2,068,456 A 1/1937 Hooper
2,275,425 A 3/1942 Grabec
(Continued)

FOREIGN PATENT DOCUMENTS

EP 0494112 A2 7/1992
EP 0598970 A1 6/1994
(Continued)

OTHER PUBLICATIONS http://palaeo.gly.bris.ac.uk/Palaeofiles/Fossilgroups/Chondrichthyes/Fossilforms/fossilforms.html (dated 2004, retrieved Oct. 16, 2013).*
U.S. Appl. No. 13/094,195, filed Apr. 26, 2011, Kirk Wallace Lake et al.
(Continued)

Primary Examiner — Timothy Kennedy
(74) Attorney, Agent, or Firm — Jeffrey V Bamber; Leonard W Lewis

(57) ABSTRACT

A method for making apertures in a web comprising providing a precursor web material; providing a pair of counter-rotating, intermeshing rollers, wherein a first roller comprises circumferentially-extending ridges and grooves, and a second roller comprises teeth being tapered from a base and a tip, the teeth being joined to the second roller at the base, the base of the tooth having a cross-sectional length dimension greater than a cross-sectional width dimension; and moving the web material through a nip of the counter-rotating, intermeshing rollers; wherein apertures are formed in the precursor web material as the teeth on one of the rollers intermesh with grooves on the other of the rollers.

27 Claims, 14 Drawing Sheets

(51) Int. Cl.
*B26F 1/20* (2006.01)
*B26F 1/24* (2006.01)
*B29C 55/18* (2006.01)
*B29C 59/02* (2006.01)
*B29K 105/00* (2006.01)

(56) References Cited

U.S. PATENT DOCUMENTS

| | | |
|---|---|---|
| 2,404,758 A | 7/1946 | Teague et al. |
| 2,633,441 A | 3/1953 | Buttress |
| 2,699,208 A | 1/1955 | Schur |
| 2,748,863 A | 6/1956 | Benton |
| 2,924,863 A | 2/1960 | Chavannes |
| 3,034,180 A | 5/1962 | Greiner et al. |
| 3,073,304 A | 1/1963 | Schaar |
| 3,081,500 A | 3/1963 | Griswold et al. |
| 3,081,512 A | 3/1963 | Griswold |
| 3,097,787 A | 7/1963 | Schur |
| 3,137,893 A | 6/1964 | Gelpke |
| 3,243,488 A | 3/1966 | Hannauer, Jr. et al. |
| 3,355,974 A | 12/1967 | Carmichael |
| 3,511,740 A | 5/1970 | Sanders |
| 3,539,423 A | 11/1970 | Simison et al. |
| 3,542,634 A | 11/1970 | Such et al. |
| 3,549,742 A | 12/1970 | Benz |
| 3,566,726 A | 3/1971 | Politis |
| 3,579,763 A | 5/1971 | Sommer |
| 3,681,182 A | 8/1972 | Kalwaites |
| 3,681,183 A | 8/1972 | Kalwaites |
| 3,684,284 A | 8/1972 | Tranfield |
| 3,695,270 A | 10/1972 | Dostal |
| 3,718,059 A | 2/1973 | Clayton |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 4,035,881 A | 7/1977 | Zocher |
| 4,042,453 A | 8/1977 | Conway |
| 4,135,021 A | 1/1979 | Patchell et al. |
| 4,189,344 A | 2/1980 | Busker |
| 4,211,743 A | 7/1980 | Nauta et al. |
| 4,244,683 A | 1/1981 | Rowland |
| 4,276,336 A | 6/1981 | Sabee |
| 4,379,799 A | 4/1983 | Holmes |
| 4,397,644 A | 8/1983 | Matthews et al. |
| 4,465,726 A | 8/1984 | Holmes |
| 4,469,734 A | 9/1984 | Minto et al. |
| 4,514,345 A | 4/1985 | Johnson et al. |
| 4,528,239 A | 7/1985 | Trokhan |
| 4,529,480 A | 7/1985 | Trokhan |
| 4,588,630 A | 5/1986 | Shimalla |
| 4,609,518 A | 9/1986 | Curro et al. |
| 4,741,941 A | 5/1988 | Englebert et al. |
| 4,758,297 A | 7/1988 | Calligarich |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,842,794 A | 6/1989 | Hovis et al. |
| 4,859,519 A | 8/1989 | Cabe, Jr. et al. |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer |
| 5,143,679 A | 9/1992 | Weber et al. |
| 5,144,730 A | 9/1992 | Dilo |
| 5,151,077 A * | 9/1992 | Cole et al. ..................... 493/353 |
| 5,165,979 A | 11/1992 | Watkins et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,632 A | 9/1993 | Mende |
| 5,328,565 A | 7/1994 | Rasch et al. |
| 5,382,245 A | 1/1995 | Thompson |
| 5,383,870 A | 1/1995 | Takai et al. |
| 5,387,209 A | 2/1995 | Yamamoto et al. |
| 5,405,675 A | 4/1995 | Sawka et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,503,715 A | 4/1996 | Trokhan et al. |
| 5,508,080 A | 4/1996 | Sorimachi et al. |
| 5,518,801 A | 5/1996 | Chappell et al. |
| 5,533,991 A | 7/1996 | Kirby et al. |
| 5,534,326 A | 7/1996 | Trokhan et al. |
| 5,554,145 A | 9/1996 | Roe |
| 5,560,794 A | 10/1996 | Currie et al. |
| 5,562,645 A | 10/1996 | Tanzer et al. |
| 5,567,501 A | 10/1996 | Srinivasan et al. |
| D375,844 S | 11/1996 | Edwards et al. |
| 5,573,719 A | 11/1996 | Fitting |
| 5,575,874 A | 11/1996 | Griesbach, III et al. |
| 5,580,418 A | 12/1996 | Alikhan |
| 5,599,420 A | 2/1997 | Yeo et al. |
| 5,624,427 A | 4/1997 | Dreier et al. |
| 5,626,571 A | 5/1997 | Young et al. |
| 5,628,097 A | 5/1997 | Benson et al. |
| 5,637,194 A | 6/1997 | Ampulski et al. |
| 5,648,142 A | 7/1997 | Phillips |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro |
| 5,704,101 A | 1/1998 | Majors et al. |
| 5,709,829 A | 1/1998 | Giacometti |
| 5,714,041 A | 2/1998 | Ayers et al. |
| 5,714,107 A | 2/1998 | Levy et al. |
| 5,723,087 A | 3/1998 | Chappell et al. |
| 5,743,776 A | 4/1998 | Igaue |
| 5,743,999 A | 4/1998 | Kamps et al. |
| 5,779,965 A | 7/1998 | Bueuther et al. |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,846,636 A | 12/1998 | Ruppel et al. |
| 5,858,504 A | 1/1999 | Fitting |
| 5,879,494 A | 3/1999 | Hoff et al. |
| 5,891,544 A | 4/1999 | Chappell et al. |
| 5,895,623 A | 4/1999 | Trokhan et al. |
| 5,897,930 A | 4/1999 | Calhoun et al. |
| 5,900,122 A | 5/1999 | Huston |
| 5,906,710 A | 5/1999 | Trokhan |
| 5,914,084 A | 6/1999 | Benson et al. |
| 5,916,661 A | 6/1999 | Benson et al. |
| 5,919,177 A | 7/1999 | Georger et al. |
| 5,925,026 A | 7/1999 | Arteman et al. |
| 5,925,299 A | 7/1999 | Dierckes et al. |
| 5,935,381 A | 8/1999 | Trokhan et al. |
| 5,964,742 A | 10/1999 | McCormack et al. |
| 5,968,029 A | 10/1999 | Chappell |
| 5,986,167 A | 11/1999 | Arteman et al. |
| 5,993,432 A | 11/1999 | Lodge et al. |
| 5,998,696 A | 12/1999 | Schone |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,080,276 A | 6/2000 | Burgess |
| 6,096,016 A | 8/2000 | Tsuji et al. |
| 6,106,928 A | 8/2000 | Laurent et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,136,146 A | 10/2000 | Phan et al. |
| 6,155,083 A | 12/2000 | Goeser et al. |
| 6,168,849 B1 | 1/2001 | Braverman et al. |

(56) References Cited

U.S. PATENT DOCUMENTS

| | | |
|---|---|---|
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,332,955 B1 | 12/2001 | Meschenmoser |
| 6,383,431 B1 | 5/2002 | Dobrin et al. |
| 6,395,122 B1 | 5/2002 | Hisanaka et al. |
| 6,395,211 B1 | 5/2002 | Dettmer et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,444,089 B1 | 9/2002 | Hollmark et al. |
| 6,451,718 B1 | 9/2002 | Yamada et al. |
| 6,452,064 B1 | 9/2002 | Thoren et al. |
| 6,454,905 B1 | 9/2002 | Hollmark et al. |
| 6,458,447 B1 | 10/2002 | Cabell |
| 6,464,831 B1 | 10/2002 | Trokhan et al. |
| D466,702 S | 12/2002 | Carlson et al. |
| 6,503,370 B2 | 1/2003 | Hollmark et al. |
| 6,506,329 B1 | 1/2003 | Curro et al. |
| 6,537,936 B1 | 3/2003 | Busam et al. |
| 6,596,127 B2 | 7/2003 | Hollmark et al. |
| 6,620,485 B1 | 9/2003 | Benson et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,739,024 B1 | 5/2004 | Wagner |
| 6,787,000 B2 | 9/2004 | Burazin et al. |
| 6,794,626 B2 | 9/2004 | Kiermeier et al. |
| 6,808,791 B2 | 10/2004 | Curro et al. |
| 6,811,652 B2 | 11/2004 | Hollmark |
| 6,818,101 B2 | 11/2004 | Vinson et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,855,220 B2 | 2/2005 | Wildeman |
| 6,863,960 B2 | 3/2005 | Curro et al. |
| 6,872,274 B2 | 3/2005 | Kauschke et al. |
| 6,884,494 B1 | 4/2005 | Curro et al. |
| 6,916,438 B2 | 7/2005 | Berry |
| 6,916,969 B1 | 7/2005 | Helmfridsson et al. |
| 6,989,075 B1 | 1/2006 | Kao et al. |
| 6,991,706 B2 | 1/2006 | Lindsay et al. |
| 7,005,558 B1 | 2/2006 | Johansson et al. |
| 7,037,569 B2 | 5/2006 | Curro et al. |
| 7,147,453 B2 | 12/2006 | Boegli |
| 7,175,412 B2 | 2/2007 | Lin |
| 7,323,072 B2 | 1/2008 | Engelhart et al. |
| 7,399,378 B2 | 7/2008 | Edwards et al. |
| 7,410,683 B2 | 8/2008 | Curro et al. |
| 7,413,630 B2 | 8/2008 | Graff et al. |
| 7,423,003 B2 | 9/2008 | Volpenhein et al. |
| 7,459,180 B2 | 12/2008 | Hamdar et al. |
| 7,521,588 B2 | 4/2009 | Stone et al. |
| 7,553,532 B2 | 6/2009 | Turner et al. |
| 7,682,686 B2 | 3/2010 | Curro et al. |
| 7,732,657 B2 | 6/2010 | Hammons et al. |
| 7,811,665 B2 | 10/2010 | Manifold |
| 7,820,874 B2 | 10/2010 | Manifold |
| 7,939,168 B2 | 5/2011 | Manifold |
| 7,960,020 B2 | 6/2011 | Manifold |
| 7,967,801 B2 | 6/2011 | Hammons |
| 7,989,058 B2 | 8/2011 | Manifold |
| 7,993,317 B2 | 8/2011 | Hammons |
| 8,012,309 B2 | 9/2011 | Pare et al. |
| 8,025,966 B2 | 9/2011 | Manifold |
| 8,058,501 B2 | 11/2011 | Hammons |
| 8,152,957 B2 | 4/2012 | Edwards et al. |
| 8,158,043 B2 | 4/2012 | Gibson |
| 8,241,543 B2 | 8/2012 | O'Donnell et al. |
| 2002/0016122 A1 | 2/2002 | Curro et al. |
| 2002/0039867 A1 | 4/2002 | Curro et al. |
| 2002/0055310 A1 | 5/2002 | Falk et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0191442 A1 | 10/2003 | Bewick-Sonntag |
| 2003/0191443 A1 | 10/2003 | Taylor |
| 2004/0110442 A1 | 6/2004 | Rhim et al. |
| 2004/0121686 A1 | 6/2004 | Wong et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0161586 A1 | 8/2004 | Cree et al. |
| 2004/0229008 A1 | 11/2004 | Hoying et al. |
| 2004/0242097 A1 | 12/2004 | Hasenoehrl et al. |
| 2004/0265533 A1 | 12/2004 | Hoying et al. |
| 2004/0265534 A1 | 12/2004 | Curro et al. |
| 2005/0051290 A1 | 3/2005 | Beasley, Jr. et al. |
| 2005/0064136 A1 | 3/2005 | Turner |
| 2005/0096614 A1 | 5/2005 | Perez et al. |
| 2005/0123726 A1 | 6/2005 | Broering et al. |
| 2005/0173085 A1 | 8/2005 | Schulz |
| 2006/0019056 A1 | 1/2006 | Turner et al. |
| 2006/0063454 A1 | 3/2006 | Chung et al. |
| 2006/0087053 A1 | 4/2006 | Turner et al. |
| 2006/0151914 A1 | 7/2006 | Gerndt et al. |
| 2006/0286343 A1 | 12/2006 | Curro et al. |
| 2007/0001270 A1 | 1/2007 | Sukegawa et al. |
| 2007/0029694 A1 | 2/2007 | Cree et al. |
| 2007/0131368 A1 | 6/2007 | Xia |
| 2008/0224351 A1 | 9/2008 | Curro et al. |
| 2009/0026651 A1 | 1/2009 | Lee et al. |
| 2009/0029106 A1 | 1/2009 | Mauler et al. |
| 2010/0001434 A1 | 1/2010 | Atkin |
| 2010/0032867 A1 | 2/2010 | Schmidt |
| 2010/0201024 A1 | 8/2010 | Gibson et al. |
| 2011/0088859 A1 | 4/2011 | Hultcrantz et al. |
| 2011/0221094 A1 | 9/2011 | Gross et al. |
| 2012/0049404 A1 | 3/2012 | Gibson |
| 2012/0064280 A1 | 3/2012 | Hammons et al. |
| 2012/0064298 A1 | 3/2012 | Orr et al. |
| 2012/0273990 A1 | 11/2012 | O'Donnell et al. |
| 2012/0276331 A1 | 11/2012 | Orr et al. |
| 2012/0276341 A1 | 11/2012 | Lake et al. |
| 2012/0282436 A1 | 11/2012 | Coe et al. |

FOREIGN PATENT DOCUMENTS

| | | |
|---|---|---|
| EP | 0 509 012 B1 | 7/1995 |
| EP | 0 955 159 A1 | 11/1999 |
| EP | 0 963 747 A1 | 12/1999 |
| EP | 1 004 412 A1 | 5/2000 |
| EP | 1440197 B1 | 1/2005 |
| FR | 1302937 A | 9/1962 |
| WO | WO 95/15138 | 6/1995 |
| WO | WO 02/100632 A1 | 12/2002 |
| WO | WO-2004/108037 A1 | 3/2004 |
| WO | WO 2005/011936 A1 | 2/2005 |
| WO | WO-2007/001270 A1 | 1/2007 |
| WO | WO-2010/135503 A1 | 11/2010 |

OTHER PUBLICATIONS

U.S. Appl. No. 13/546,015, filed Jul. 11, 2012, Hugh Joseph O'Donnell et al.

U.S. Appl. No. 13/455,857, filed Apr. 25, 2012, Richard George Coe et al.

U.S. Appl. No. 13/455,925, filed Apr. 25, 2012, Jill Marlene et al.

* cited by examiner

METHOD AND APPARATUS FOR MAKING AN APERTURED WEB

CROSS REFERENCE TO RELATED APPLICATION

This application is a continuation of U.S. application Ser. No. 11/249,618, filed Oct. 13, 2005, now U.S. Pat. No. 8,241,543 which is a continuation in part of U.S. application Ser. No. 10/913,199, filed Aug. 6, 2004 (abandoned), which claims the benefit of U.S. provisional application No. 60/493,207, filed Aug. 7, 2003.

FIELD OF THE INVENTION

The present invention relates to methods and apparatus for making apertured webs. Specifically, the method and apparatus can be used to make three-dimensional apertured films, nonwovens, and laminates thereof.

BACKGROUND OF THE INVENTION

Apertured webs are utilized in a wide variety of industrial and consumer products. For example, apertured films or apertured nonwovens are known for use in disposable absorbent articles such as disposable diapers and feminine hygiene articles such as sanitary napkins, and the like. Such articles typically have a fluid pervious topsheet, a fluid impervious backsheet, and an absorbent core disposed between the topsheet and the backsheet.

Methods of making apertured nonwoven webs for use as topsheets in disposable absorbent articles are known. For example, U.S. Pat. No. 5,628,097, issued to Benson et al. on May 13, 1997, discloses a method of making weakened melt stabilized locations that are subsequently ruptured by a tensioning force to produce apertures. Other methods, such as slitting and stretching, hot pin aperturing are likewise well known in the art.

Methods for making perforated polymer films are also known. For example, U.S. Pat. No. 2,748,863 discloses the use of a perforating cylinder studded with hot pins arranged in annular rows and an anvil roller having grooves that cooperate with the pins in defining a nip wherein thermoplastic films can be perforated. However, such processes are not disclosed as making three-dimensional apertured webs beyond that of simple material displacement such as an annular ring round the perforations.

When used in feminine hygiene articles as a topsheet (or secondary topsheet, as is known in the art of feminine hygiene articles), three-dimensional formed film apertured webs can have improved functionality because the three-dimensionality provides a degree of "stand off" between the users body and an underlying absorbent core component. Various methods of making three-dimensional formed film apertured webs for use as topsheets are known. For example, vacuum forming methods are utilized to make macroscopically expanded, three dimensional, apertured polymeric webs are disclosed in U.S. Pat. No. 4,342,314 issued to Radel et al. on Aug. 3, 1982 and U.S. Pat. No. 4,463,045 issued to Ahr et al. on Jul. 31, 1984.

Other methods for making three-dimensional formed film apertured webs are known, such as hydroforming as disclosed in U.S. Pat. No. 4,609,518, issued Sep. 2, 1986, U.S. Pat. No. 4,629,643, issued Dec. 16, 1986, and U.S. Pat. No. 4,695,422, issued Sep. 22, 1987, all in the name of Curro et al.

Whether using vacuum as disclosed in Radel et al. or Ahr et al., or hydroforming as disclosed in Curro et al., current processes for making apertured webs, particularly apertured three-dimensional formed film webs, are relatively expensive due to the energy-intensive processes and the capital expenditures necessary for carrying out such processes. Further, for use in disposable articles, the webs cannot be manufactured as part of the process for manufacturing the disposable article. Typically such webs are made in a separate process and stored as roll stock that can tend to destroy or diminish the original three-dimensionality of the web.

Accordingly, there is a need for a less costly method for making apertured webs, including three-dimensional apertured formed film webs.

Further, there is a need for a method and apparatus for making apertured webs that can be incorporated into manufacturing lines for disposable articles, such that the webs need not be stored as roll stock after manufacture.

Further, there is a need for a method and apparatus for making three-dimensional apertured webs that does not require energy-intensive vacuum and/or hydroforming steps.

Further, there is a need for a method and apparatus for making three-dimensional formed film apertured webs suitable for use as a topsheet in a disposable absorbent article, wherein the method and apparatus do not require vacuum or fluid pressure to form the three-dimensional apertures.

SUMMARY OF THE INVENTION

A method for making apertures in a web is disclosed. The method comprises providing a precursor web material; providing a pair of counter-rotating, intermeshing rollers, wherein a first roller comprises circumferentially-extending ridges and grooves, and a second roller comprises teeth being tapered from a base and a tip, the teeth being joined to the second roller at the base, the base of the tooth having a cross-sectional length dimension greater than a cross-sectional width dimension; and moving the web material through a nip of the counter-rotating, intermeshing rollers; wherein apertures are formed in the precursor web material as the teeth on one of the rollers intermesh with grooves on the other of the rollers.

DETAILED DESCRIPTION OF THE INVENTION

An apertured web 1 of the present invention will be described with respect to a method and apparatus of making, also of the present invention. Apertured web can be an apertured film, and apertured nonwoven web, or a laminate thereof. Apertures can include micro apertures and macro apertures, the former being substantially invisible to the unaided naked eye of an observer from approximately 1 meter away in ordinary indoor lighting and the latter being visible under such conditions. Micro apertures and/or other embossing or texturing can be formed prior to processing by the apparatus of the present invention.

Figure 1:
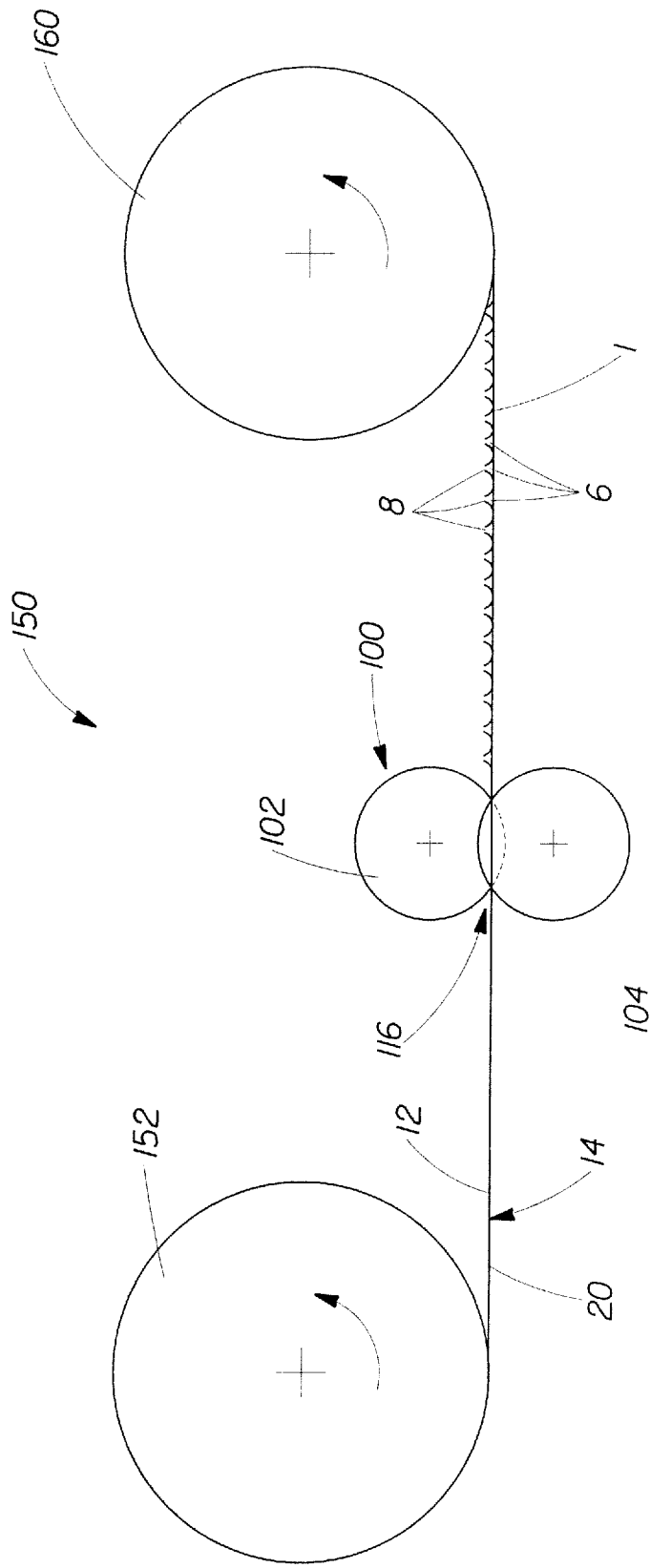
FIG. 1 is a schematic representation of a process of the present invention.

One apparatus 150 of the present invention is shown schematically in FIG. 1. As shown in FIG. 1, web 1 can be formed from a generally planar, two dimensional precursor web 20 having a first surface 12 and a second surface 14. Precursor web 20 can be can be, for example, a polymer film, a nonwoven web, a woven fabric, a paper web, a tissue paper web, or a knitted fabric, or a multilayer laminate of any of the aforementioned. First surface 12 corresponds to a first side of precursor web 20, as well as a first side of web 1. Second surface 14 corresponds to a second side of precursor web 20, as well as a first side of web 1. In general, the term "side" is used herein in the common usage of the term to describe the two major surfaces of generally two-dimensional webs, such as paper and films. Of course, in a composite or laminate structure, the first surface 12 of the web 1 is the first side of one of the outermost layers or plies, and the second surface 14 is the second side of the other outermost layer or ply.

Precursor web 20 can be a polymeric film web. In one embodiment precursor web 20 can be a polymeric web suitable for use as a topsheet in a disposable absorbent product, as is known in the art. Polymeric film webs can be deformable. Deformable material as used herein describes a material which, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials. The processes of the present invention are used to form materials comprising a polymeric film. Such materials include polymeric films alone or laminates comprising polymeric films and other materials.

Deformable polymeric film webs utilized in the process of the present invention can have a transformation temperature range where changes in the solid state molecular structure of the material occur, such as a change in crystalline structure or a change from solid to molten state. As a consequence, above the transformation temperature range, certain physical properties of the material are substantially altered. For a thermoplastic film, the transformation temperature range is the melt temperature range of the film, above which the film is in a molten state and loses substantially all previous thermo-mechanical history.

Polymeric film webs can comprise thermoplastic polymers having characteristic rheological properties which depend on their composition and temperature. Below their glass transition temperature, such thermoplastic polymers can be quite hard and stiff and often brittle. Below this glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. In one embodiment, the processes of the present invention can be utilized to form materials comprising thermoplastic polymer, especially thermoplastic film, which is within this viscoelastic temperature range.

Polymeric film webs can comprise a certain amount of ductility. Ductility, as used herein, is the amount of permanent, unrecoverable, plastic strain which occurs when a material is deformed, prior to failure (rupture, breakage, or separation) of the material. Materials formed in the process of the present invention can have a minimum ductility of at least about 10%, or at least about 50%, or at least about 100%, or at least about 200%.

Polymeric film webs utilized in the present invention can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. As noted below, polymeric film webs can be textured, embossed, or otherwise altered from a strictly flat, planar configuration.

Precursor web 20 can also be a nonwoven web. For nonwoven precursor webs 20, the precursor web can comprise unbonded fibers, entangled fibers, tow fibers, or the like, as is known in the art for nonwoven webs. Fibers can be extensible and/or elastic, and may be pre-stretched for processing by apparatus 150. Fibers of precursor web 20 can be continuous, such as those produced by spunbonded methods, or cut to length, such as those typically utilized in a carded process. Fibers can be absorbent, and can include fibrous absorbent gelling materials (fibrous AGM). Fibers can be bicomponent, multiconstituent, shaped, crimped, or in any other formulation or configuration known in the art for nonwoven webs and fibers.

Nonwoven precursor webs 20 can be any known nonwoven webs comprising polymer fibers having sufficient elongation properties to be formed into web 1 as described more fully below. In general, the polymeric fibers can be bondable, either by chemical bond, i.e., by latex or adhesive bonding, pressure bonding, or thermal bonding. If thermal bonding techniques are used in the bonding process described below, a certain percentage of thermoplastic material, such as thermoplastic powder or fibers can be utilized as necessary to facilitate thermal bonding of portions of fibers in the web, as discussed more fully below. Nonwoven precursor web 20 can comprise 100% by weight thermoplastic fibers, but it can comprise as low as 10% by weight thermoplastic fibers. Likewise, nonwoven precursor web 20 can comprise any amount by weight thermoplastic fibers in 1% increments between about 10% and 100%.

Precursor web 20 can be a composite or a laminate of two or more precursor webs, and can comprise, for example, two or more nonwoven webs or a combination of polymer films, nonwoven webs, woven fabrics, paper webs, tissue webs, or knitted fabrics. Precursor web 20 can be supplied from a supply roll 152 (or supply rolls, as needed for multiple web laminates) or any other supply means, such as festooned webs, as is known in the art. In one embodiment, precursor web 20 can be supplied directly from a web making apparatus, such as a polymer film extruder or a nonwoven web-making production line.

As used herein, the term "nonwoven web" refers to a web having a structure of individual fibers or threads which are interlaid, but not in a repeating pattern as in a woven or knitted fabric, which do not have randomly oriented fibers. Nonwoven webs or fabrics have been formed from many known processes, such as, for example, air laying processes, meltblowing processes, spunbonding processes, hydroentangling processes, spunlacing processes, and bonded carded web processes. Also, multi-layer webs, such as spunbond-meltblown-spunbond (SMS) webs and the like (e.g., SMMS, SSMS) made by multiple beam spunbond processes, can be utilized. It is not necessary that each component (i.e., the spunbond or meltblown components) be the same polymer. Therefore, in an SMS web, it is not necessary that the spunbond and the meltblown layers comprise the same polymer.

The basis weight of nonwoven fabrics is usually expressed in grams per square meter (gsm) (or equivalent, such as oz/sq yard) and the fiber diameters are usually expressed in microns. Fiber size can also be expressed in denier. The total basis weight of precursor web 20 (including laminate or multi-layer precursor webs 20) can range from 8 gsm to 500 gsm, depending on the ultimate use of the web 1, and can be produced in 1 gsm increments between 8 and 500 gsm. For use as a hand towel, for example, a basis weight of precursor web 20 of between 25 gsm and 100 gsm may be appropriate. For use as a bath towel a basis weight of between 125 gsm and 250 gsm may be appropriate. For use as an air filter, including a High Efficiency Particulate Air (HEPA) filter, useful in air cleaning equipment including dust collectors, nuclear and biological filters, and some types of gas turbine inlet air filtration, a basis weight of between 350 gsm and 500 gsm may be appropriate (pleated and ganged, if necessary to increase effective surface area). The constituent fibers of nonwoven precursor web 20 can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from 0.1-500 microns in 1 micron increments.

As used herein, "spunbond fibers" is used in its conventional meaning, and refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" is used in its conventional meaning, and refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" is used in its conventional meaning, and generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries. In general, any of the known polymer types can be utilized in the present invention, for example, polyolefinic polymers such as polypropylene or polyethylene can be used either as monocomponent fibers or bicomponent fibers. Additionally, other polymers such as PVA, PET polyesters, metallocene catalyst elastomers, nylon and blends thereof can be used, any or all of which polymers can be cross linked if desired.

As used herein, the term "monocomponent" fiber is used in its conventional meaning, and refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" is used in its conventional meaning, and refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer (such as polypropylene) is surrounded by another (such as polyethylene), or may be a side-by-side arrangement, a pie arrangement, or an "islands-in-the-sea" arrangement, each as is known in the art of multicomponent, including bicomponent, fibers.

Fibers, including bicomponent fibers, can be splittable fibers, such fibers being capable of being split lengthwise before or during processing into multiple fibers each having a smaller cross-sectional dimension than the original bicomponent fiber. Splittable fibers have been shown to produce softer nonwoven webs due to their reduced cross-sectional dimensions. Fibers can be nanofibers, i.e., fibers having a diameter in the sub-micron range up to and including the low micron range.

As used herein, the term "biconstituent fibers" is used in its conventional meaning, and refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "shaped fibers" is used in its conventional meaning, and describes fibers having a non-round cross-section, and include "capillary channel fibers." Such fibers can be solid or hollow, and they can be tri-lobal, delta-shaped, and are preferably fibers having longitudinally-extending grooves that serve as capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

Precursor web 20 is moved in a machine direction (MD) for forming apertures therein by forming apparatus 150. Machine direction (MD) refers to the direction of travel for precursor web 20 as is commonly known in the art of making or processing web materials. Likewise, cross machine direction (CD) refers to a direction perpendicular to the MD, in the plane of precursor web 20.

Precursor web 20 can be provided either directly from a web making process or indirectly from a supply roll 152, as shown in FIG. 1. Precursor web 20 can be preheated by means known in the art, such as by radiant heating, forced air heating, convection heating, or by heating over oil-heated rollers. Precursor web 20 can be pre-printed with indicia, designs, logos, or other visible or invisible print patterns. For example, designs and colors can be printed by means known in the art, such as by ink-jet printing, gravure printing, flexographic printing, or offset printing, to change the color of at least portions of precursor web 20. In addition to printing, precursor web 20 can be treated with coatings, such as with surfactants, lotions, adhesives, and the like. Treating precursor web 20 can be achieved by means known in the art such as by spraying, slot coating, extruding, or otherwise applying coatings to one or both surfaces.

Supply roll 152 rotates in the direction indicated by the arrow in FIG. 1 as precursor web 20 is moved in the machine direction by means known in the art, including over or around any of various idler rollers, tension-control rollers, and the like (all of which are not shown) to the nip 116 of a pair of counter-rotating, intermeshing rolls 102 and 104. The pair of intermeshing rolls 102 and 104 operate to form apertures in web 1. Intermeshing rolls 102 and 104 are more clearly shown in FIG. 2.

Figure 2:
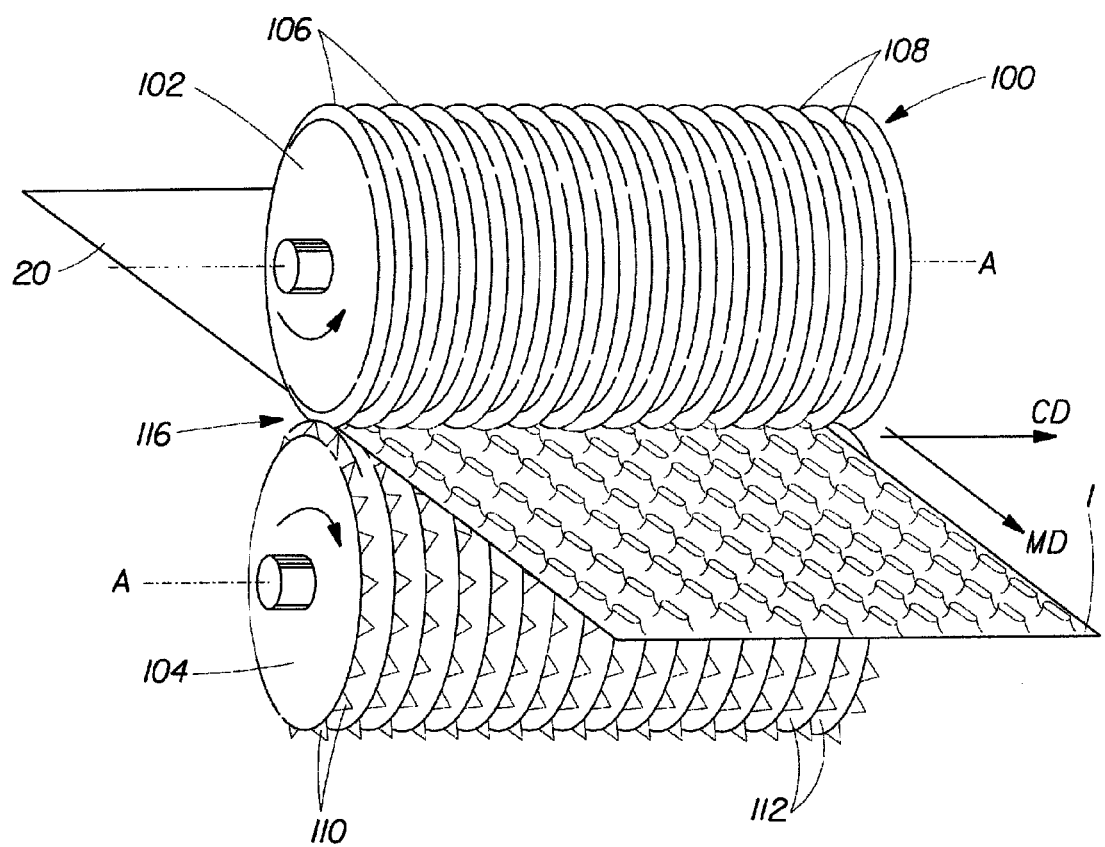
FIG. 2 is perspective representation of an apparatus of the present invention.
Figure 8:
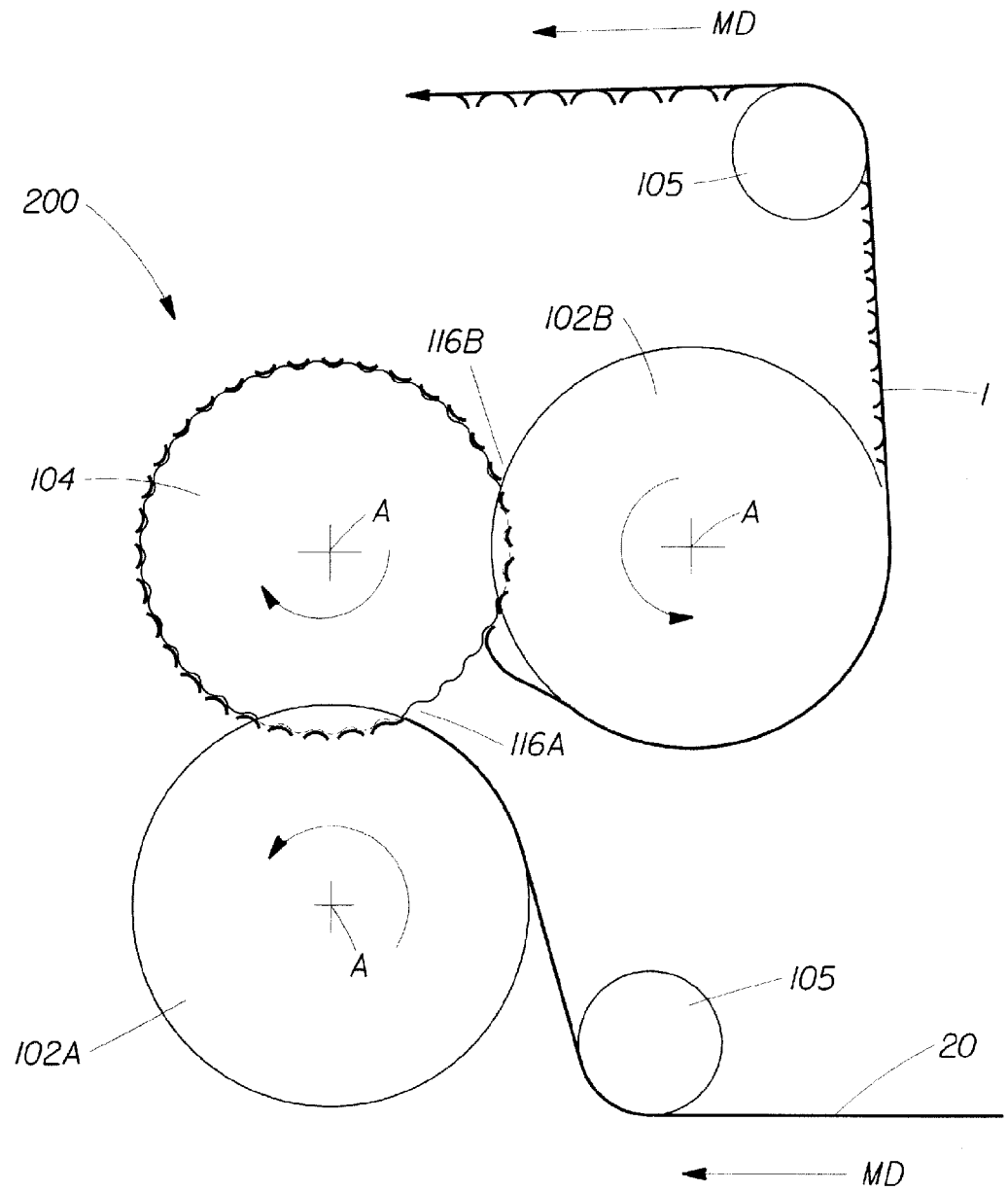
FIG. 8 is a schematic representation of another embodiment of a process and apparatus of the present invention.

Referring to FIG. 2, there is shown in more detail the portion of forming apparatus 150 for making apertures in apertured web 1. This portion of apparatus 150 is shown as forming apparatus 100 in FIG. 2, and comprises a pair of steel intermeshing rolls 102 and 104, each rotating about an axis A, the axes A being parallel and in the same plane. Forming apparatus 100 can be designed such that precursor web 20 remains on roll 104 through a certain angle of rotation, as shown in detail below with respect to FIG. 8, but FIG. 2 shows in principle what happens as precursor web 20 goes straight through nip 116 on forming apparatus 100 and exits as apertured web 1. Therefore, while FIG. 2 shows apertured web 1 going straight into and coming straight out of nip 116, precursor web 20 or apertured web 1 can be partially wrapped on either of rolls 102 or 104 through a predetermined angle of rotation prior to (for precursor web 20) or after (for apertured web 1) nip 116. For example, after exiting nip 116, apertured web 1 can directed to be wrapped on roll 104 through a predetermined angle of rotation such that the apertures remain resting over, and "fitted" onto, teeth 110 of roll 104, as shown in FIG. 8.

Figure 2A:
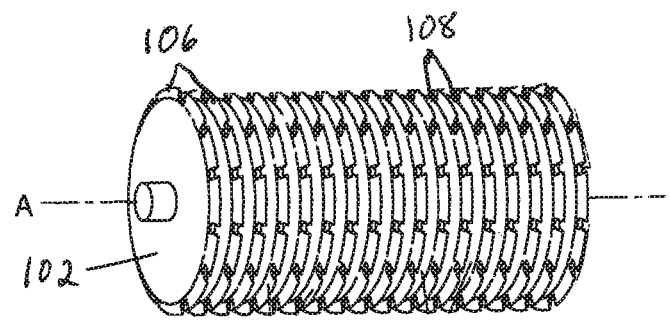
FIG. 2A is a perspective view of an alternative embodiment of a roll having ridges with breaks therein.
Figure 2B:
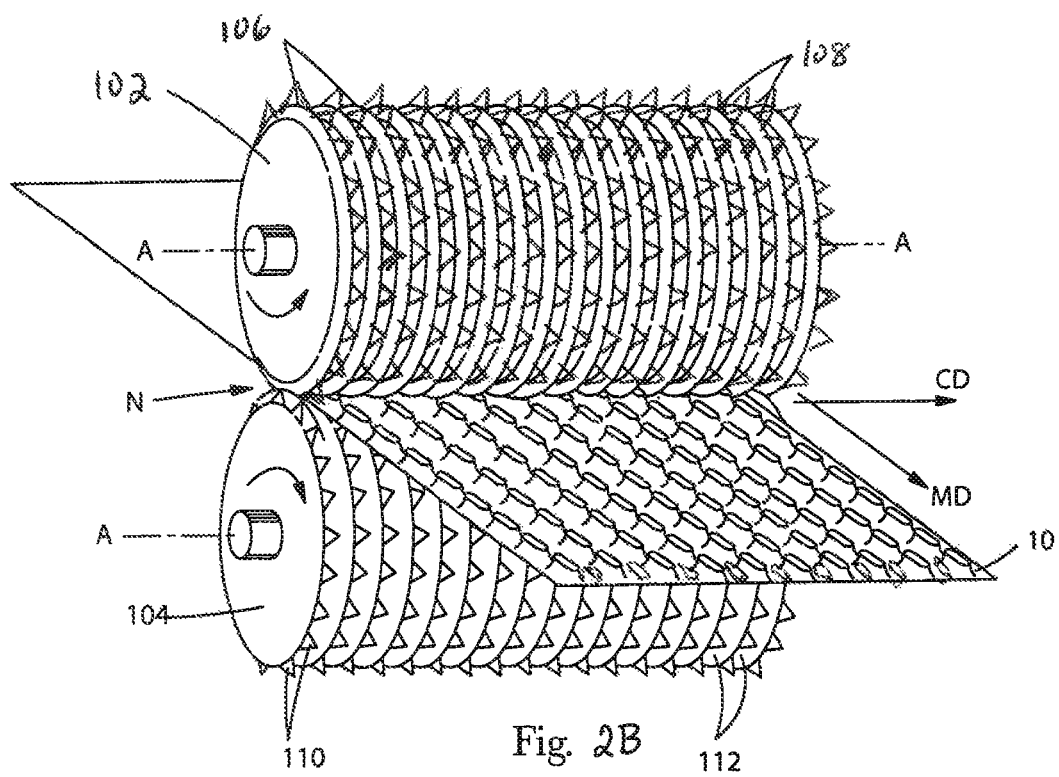
FIG. 2B is a perspective view of an alternative embodiment showing a pair of rolls, each of which have teeth thereon.

Roll 102 can comprise a plurality of ridges 106 and corresponding grooves 108 which can extend unbroken about the entire circumference of roll 102. In some embodiments, depending on what kind of pattern is desired in web 1, roll 102 can comprise ridges 106 wherein portions have been removed, such as by etching, milling or other machining processes, such that some or all of ridges 106 are not circumferentially continuous, but have breaks or gaps, an example of which is shown in FIG. 2A. The breaks or gaps can be arranged to form a pattern, including simple geometric patterns such as circles or diamonds, but also including complex patterns such as logos and trademarks. In one embodiment, such as shown in FIG. 2B, roll 102 can have teeth, similar to the teeth 110 on roll 104, described more fully below. In this manner, it is possible to have three dimensional apertures having portions extending outwardly on both sides of apertured web 1. In addition to apertures, various out-of-plane macro-areas of apertured of web 1 can be made, including macro-patterns of embossed texture depicting logos and/or designs.

Roll 104 is similar to roll 102, but rather than having ridges that can extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 7, discussed below. Both or either of rolls 102 and 104 can be heated by means known in the art such as by incorporating hot oil filled rollers or electrically-heated rollers. Alternatively, both or either of the rolls may be heated by surface convection or by surface radiation.

Teeth 110 can be joined to roller 104. By "joined" is meant that teeth can be attached to, such as by welding, compression fit, or otherwise joined. However, "joined" also includes integral attachment, as is the case for teeth machined by removing excess material from roller 104. The location at which teeth 110 are joined to roller 104 is the base. At any cross-sectional location parallel to the base each tooth can have a non-round cross-sectional area. In the circumferential direction a cross-sectional length of the cross-sectional area (corresponding to the tooth length, as discussed below), is at least two times a cross sectional width, measured perpendicular to the length dimension at the center of the cross-sectional area.

Rollers 102 and 104 can be made of steel. In one embodiment, the rollers can be made of stainless steel. In general, rollers 102 and 104 can be made of corrosion resistant and wear resistant steel.

Figure 3:
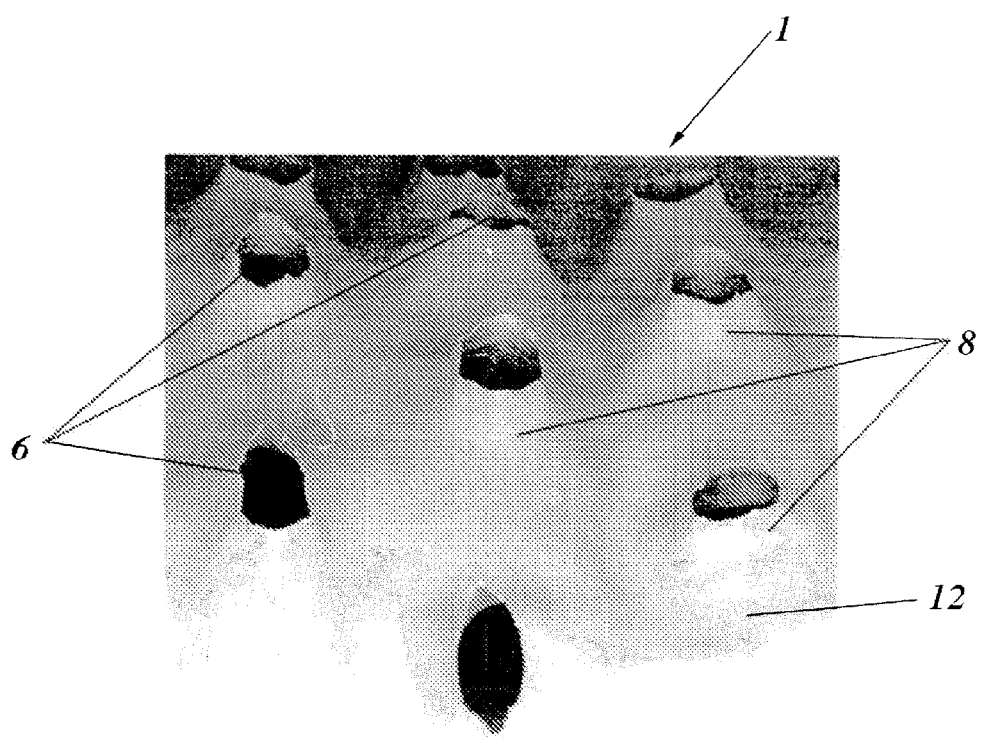
FIG. 3 is a photograph of a highly magnified portion of an apertured web made by the process of the present invention.

Two representative three-dimensional apertured formed film webs 1 are shown in the photomicrographs of FIGS. 3-6. FIG. 3 shows a portion of a three-dimensional, apertured formed film web 1 made from a generally planar polyethylene film precursor web 20 having a basis weight of approximately 25 grams per square meter. Apertures 6 shown in FIG. 3 were formed by the action of teeth 110 on a heated roll 104 having stretched and pushed through precursor web 20 to permanently deform precursor web 20 to form a plurality of discrete, spaced apart volcano-like structures 8 extending outwardly from first side 12. Webs as shown in FIGS. 3-6 can be made by processing through the nip 116 of rolls 102 and 104 heated to about 200° F. In general, line speed and sufficient heating of apparatus 100 depends on the size of teeth 110, the angle of wrap on either roll, and/or the type and basis weight of the precursor web 20, all of which can be varied as necessary by means well known in the art.

Figure 4:
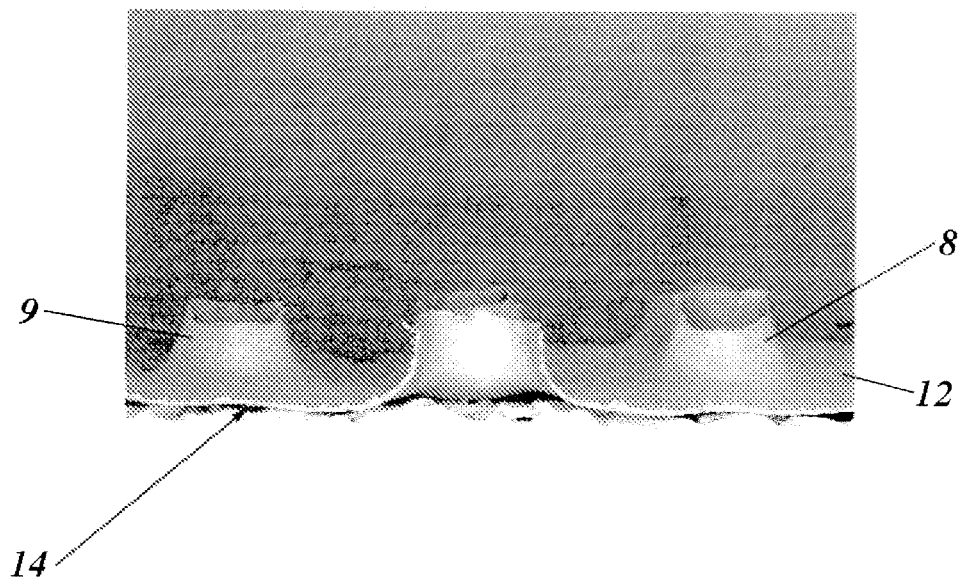
FIG. 4 is a cross-sectional view of the apertured web of FIG. 3.

As shown in the cross section of FIG. 4, apertures 6 place the first side 12 and the second side 14 of web 1 in fluid communication through the volcano-like structures 8. Volcano-like structures 8 comprise a continuous side wall 9 of deformed film having a significant orientation in the Z-direction which can be relatively rigid to resist Z-direction compression in use. The undeformed portions of apertured web 1 of FIGS. 3 and 4 can be fluid impervious.

The number of apertures 6 per unit area of apertured web 1, i.e., the area density of apertures 6, can be varied from 1 aperture 6 per square centimeter to as high as 60 apertures 6 per square centimeter. There can be at least 10, or at least 20 apertures 6 per square centimeter, depending on the end use. In general, the area density need not be uniform across the entire area of web 1, but apertures 6 can be only in certain regions of apertured web 1, such as in regions having predetermined shapes, such as lines, stripes, bands, circles, and the like. In one embodiment, where web 1 is used as a topsheet for a sanitary napkin, for example, apertures 6 can be only in the region corresponding to the central part of the pad where fluid entry occurs.

As can be understood with respect to apparatus 100, therefore, apertures 6 of apertured web 1 are made by mechanically deforming precursor web 20 that can be described as generally planar and two dimensional. By "planar" and "two dimensional" is meant simply that the web is flat relative to the finished web 1 that has distinct, out-of-plane, Z-direction three-dimensionality imparted due to the formation of volcano-shaped structures 8. "Planar" and "two-dimensional" are not meant to imply any particular flatness, smoothness or dimensionality. As such, a soft, fibrous non-woven web can be planar in its as-made condition. As precursor web 20 goes through the nip 116 the teeth 110 of roll 104 enter grooves 108 of roll 102 and simultaneously urge material out of the plane of precursor web 20 to form permanent volcano-like structures 8 and apertures 6. In effect, teeth 110 "push" or "punch" through precursor web 20. As the tip of teeth 110 push through precursor web 20 the web material is urged by the teeth 110 out of the plane of precursor web 20 and is stretched and/or plastically deformed in the Z-direction, resulting in formation of permanent volcano-like structures 8 and apertures 6. The amount of ductility and other material properties of the precursor web, such as the glass transition temperature determine how much relatively permanent three-dimensional deformation web 1 retains.

Figure 5:
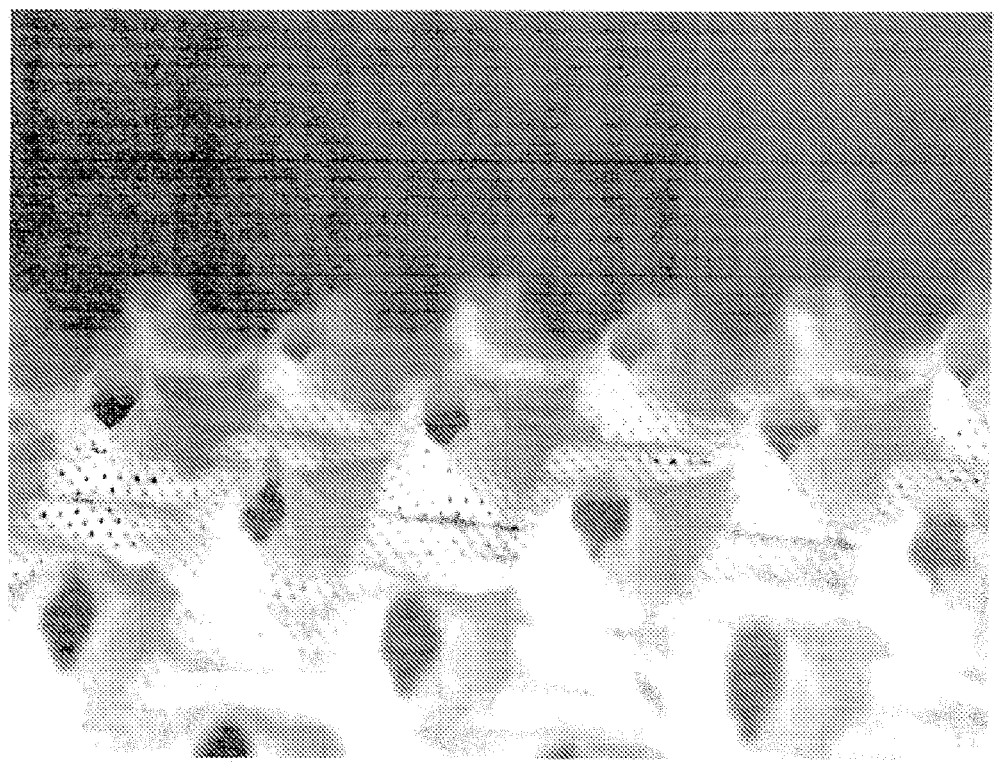
FIG. 5 is a photograph of a highly magnified portion of an apertured web made by the process of the present invention.
Figure 6:
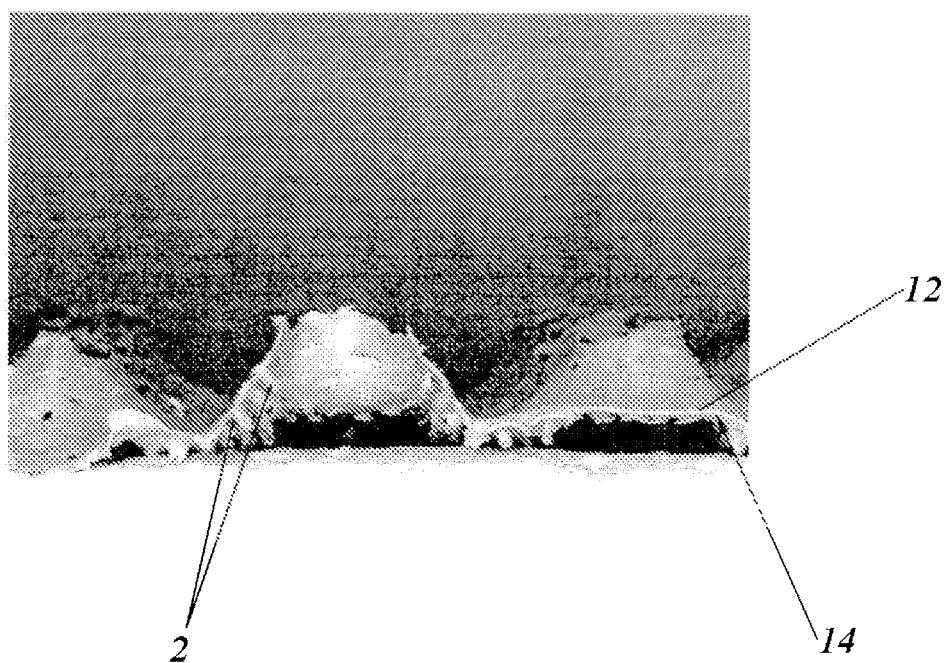
FIG. 6 is a cross-sectional view of the apertured web of FIG. 5.

FIGS. 5 and 6 show another embodiment of a three-dimensional apertured web 1 in which the precursor web 20 was not a flat film but rather was a film that was pre-textured with microscopic aberrations 2. Aberrations 2 can be bumps, embossments, holes, or the like. In the embodiment shown, aberrations 2 are also volcano-shaped micro-apertures, formed by a hydroforming process. A suitable hydroforming process is the first phase of the multiphase hydroforming process disclosed in U.S. Pat. No. 4,609,518, issued to Curro et al. on Sep. 2, 1986. The hydroforming screen utilized for the webs shown in FIGS. 5 and 6 was a "100 mesh" screen and the film was obtained from Tredegar Film Products, Terre Haute, Ind. Apertures 6 were formed by teeth 110 of roll 104 in apparatus 100.

As shown in the cross section of FIG. 6, in one embodiment apertures 6 formed by the teeth 110 of roll 104 extend in a direction away from first side 12 while the aberrations 2 such as the micro apertures formed by hydroforming extend away from second side 14. Aberrations 2 can also be non-apertured protrusions, fibrils, or embossments to provide texture that provides for a tactile impression of softness. Softness is beneficial when webs 1 are used as topsheets in disposable absorbent articles, and the method disclosed herein for forming volcano-shaped structures 8 and apertures 6 is effective in preserving the micro texture aberrations 2, particularly when the volcano-shaped structures 8 and apertures 6 are made on the disposable absorbent article production line. In this manner, a soft, compliant topsheet for a disposable absorbent article can be achieved when the web 1 is used with the second side 14 having aberrations 2 as the body-facing surface of the article.

The apertures 6 of the film embodiments shown in FIGS. 3-6 were made on an apparatus like that shown in FIG. 2, where the apparatus 100 is arranged to have one patterned roll, e.g., roll 104, and one non-patterned grooved roll 102. However, in certain embodiments it may be preferable to form nip 116 by use of two patterned rolls having either the same or differing patterns, in the same or different corresponding regions of the respective rolls. Such an apparatus can produce webs with apertures 6 protruding from both sides of the apertured web 1, as well as macro-texture, e.g., aberrations, micro-apertures, or micro-patterns, embossed into the web 1. Likewise, it may be desirable to have multiple apparatuses 100 such that web 1 is re-processed to have additional structures 8 and/or apertures 6. For example, a higher area density of volcano-shaped structures 8 on web 1 can be achieved by processing precursor web 20 through two or more apparatuses 100.

The number, spacing, and size of apertures 6 can be varied by changing the number, spacing, and size of teeth 110 and making corresponding dimensional changes as necessary to roll 104 and/or roll 102. This variation, together with the variation possible in precursor webs 20 and the variation in processing, such as line speeds, roll temperature, and other post processing variations, permits many varied apertured webs 1 to be made for many purposes. Apertured web 1 can be used in disposable absorbent articles such as bandages, wraps, incontinence devices, diapers, sanitary napkins, pantiliners, tampons, and hemorrhoid treatment pads, as well as other consumer products such as floor cleaning sheets, body wipes, and laundry sheets. In addition, webs 1 of the present invention can be utilized as perforated webs in automotive, agricultural, electrical, or industrial applications.

Figure 7:
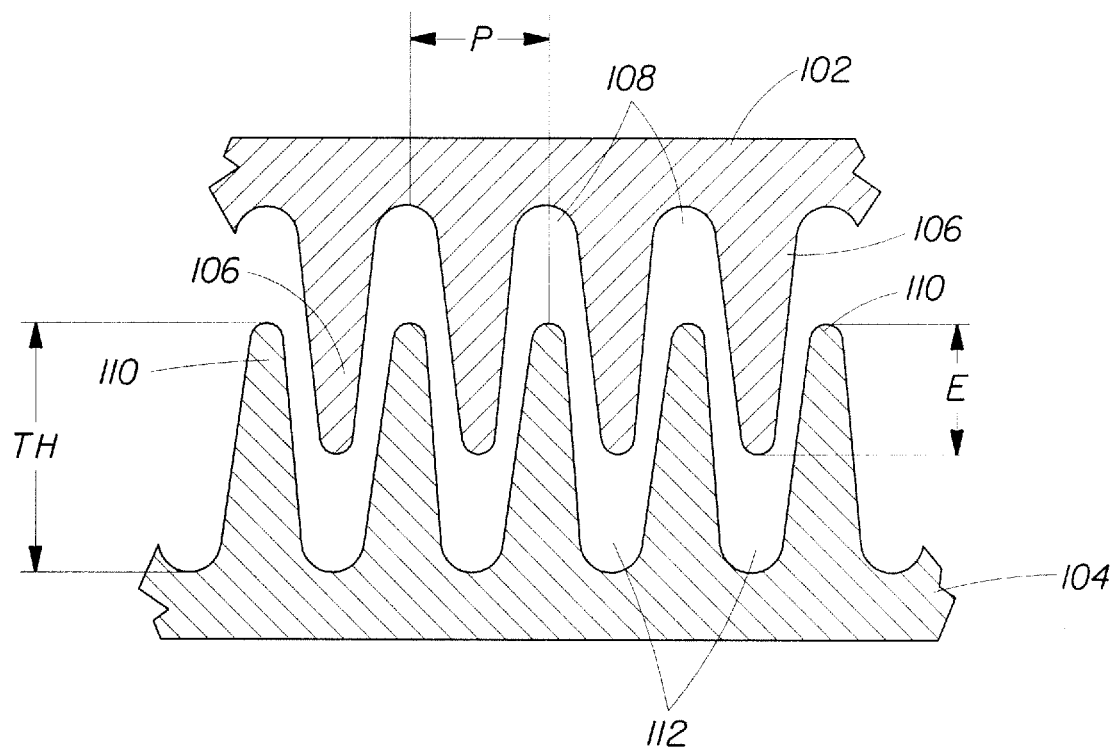
FIG. 7 is a cross-sectional representation of a portion of the apparatus shown in FIG. 2.

FIG. 7 shows in cross section a portion of the intermeshing rolls 102 and 104 including ridges 106 and representative teeth 110. As shown, teeth 110 have a tooth height TH (note that TH can also be applied to ridge 106 height; in a preferred embodiment tooth height and ridge height are equal), and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 110. The depth of engagement E, tooth height TH, and pitch P can be varied as desired depending on the properties of precursor web 20 and the desired characteristics of web 1 of the present invention. For example, in general, to obtain a higher density of volcano-shaped structures 8 or apertures 6 of web 1, the smaller the pitch should be, and the smaller the tooth length TL and tooth distance TD should be, as described below.

In one embodiment, web 1 can be formed by processing a precursor web 20 through an apparatus 200 as shown in FIG. 8. The multi-roller arrangement of apparatus 200 is designed to provide for a predetermined dwell time in which apertured web 1 remains in contact with toothed roller 104 through a predetermined angle of rotation. While the angle of rotation can be optimized depending upon the type of film, temperature of rollers, and the speed of web travel, in general the angle of wrap can be at least 10 degrees and as high as about 270 degrees or more, depending, at least in part, on the relative sizes of the mating rollers. As shown, precursor web 20 can be guided around various guide rollers and tensioning members (not shown) to guide roller 105 and onto roll 102A which can have ridges and grooves as described with respect to roller 102 of apparatus 150 in FIG. 1 above. Roller 102A can be heated to aid in forming volcano-shaped structures 8 and apertures 6. In one embodiment, roller 102 can be heated to about 200° F.

Precursor web 20 enters nip 116A formed by the inter-engagement of meshing rollers 104 and 102A. Roller 104 of apparatus 200 can be a toothed roller as described above with respect to apparatus 150 in FIG. 1. As precursor web 20 passes through nip 116A, teeth 110 on roller 104 press into and/or through and can pierce precursor web 20 to form volcano-shaped structures 8 and apertures 6. Apertured web 1 then continues in stationary contact with rotating roller 104 until reaching nip 116B formed by the inter-engagement of roller 104 with roller 102B. Roller 102B can have ridges and grooves as described with respect to roller 102 of apparatus 150 in FIG. 1 above.

As web 1 exits nip 116B it is directed off of roller 104, onto roller 102B and over various guide rollers 105 as necessary before being wound for further processing, shipping, or placement for incorporation in a manufactured product. In one embodiment, web 1 is directed into a manufacturing process for sanitary napkins, wherein web 1 is fed into the process as a topsheet and joined to other components such as a backsheet web, cut to finished shape, packaged, and shipped to retail outlets. If web 1 tends to stick to teeth 110 upon being pulled off of roller 104, various processing aids can be added as necessary. For example, non-stick treatments, such as silicone or fluorocarbon treatments can be added. Various lubricants, surfactants or other processing aids can be added to the precursor web 20 or to the roller 104. Other methods of aiding the removal of the web from the roller include air knives or brushing. In one embodiment, roller 104 can have an internal chamber and means to provide positive air pressure at the point of web removal onto roller 102B. In general, control of the transition from roller 104 to roller 102B is affected by web speed, relative roller speeds (i.e., tangential speed of roller 104 and roller 102B), web tension, and relative coefficients of friction. Each of these parameters can be varied as known by those skilled in the art to ensure the desired transfer of web 1 onto roller 102B.

The benefit of having an apparatus like that shown in FIG. 8 is that web 1 experiences an extended amount of time in contact with and "nested" on teeth 110 of roller 104. In this manner, volcano-shaped structures 8 and apertures 6 have additional time to set and a higher likelihood of retaining a three-dimensional configuration once removed from roller 104. Without being bound by theory, it is believed that by adjusting the circumference of roller 104, the temperature of rollers 102A, 104, and/or 102B, as well as the coefficient of friction of rollers, this longer dwell time can be used to increase the line speed at which web 1 can be processed to make permanent three-dimensional volcano-shaped structures 8. The temperature of rollers 102A, 104, and/or 102B may all be at the same temperature or alternatively at different temperatures. For example, rollers 102A and 104 may be heated while roller 102B is at room temperature or below. In addition, the speeds of the various rollers may be maintained at the same speed, or alternately a speed differential between the rollers may be established.

If any of the rollers of the apparatus 150 or 200, as described above are to be heated, care must be taken to account for thermal expansion. In one embodiment, the dimensions of ridges, grooves, and/or teeth are machined to account for thermal expansion, such that the dimensions shown in FIG. 7 and dimensions described herein are dimensions at operating temperature.

Figure 9:
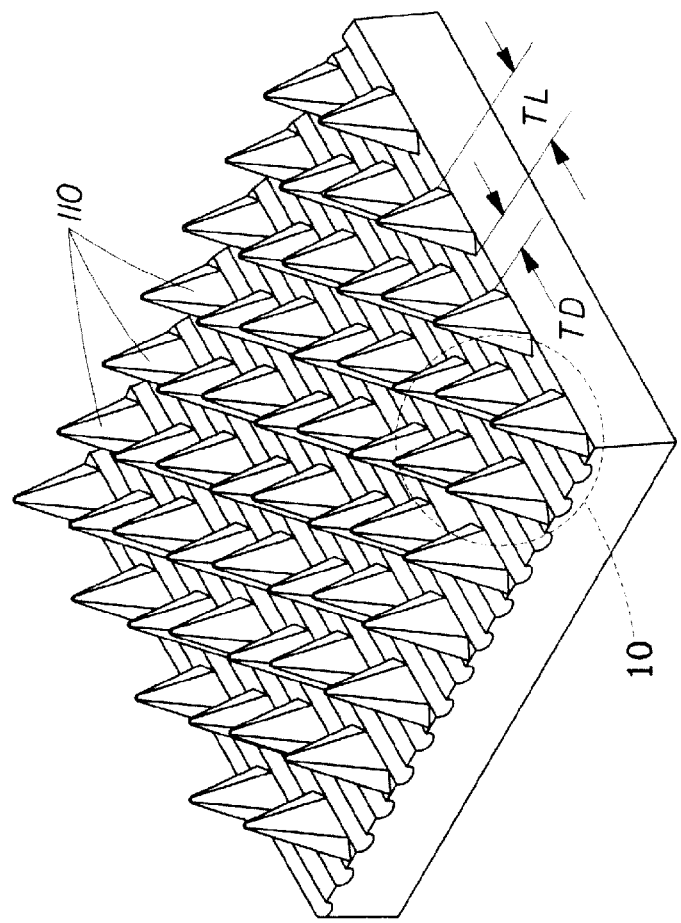
FIG. 9 is a perspective view of a portion of the apparatus shown in FIG. 2 or FIG. 8.
Figure 10:
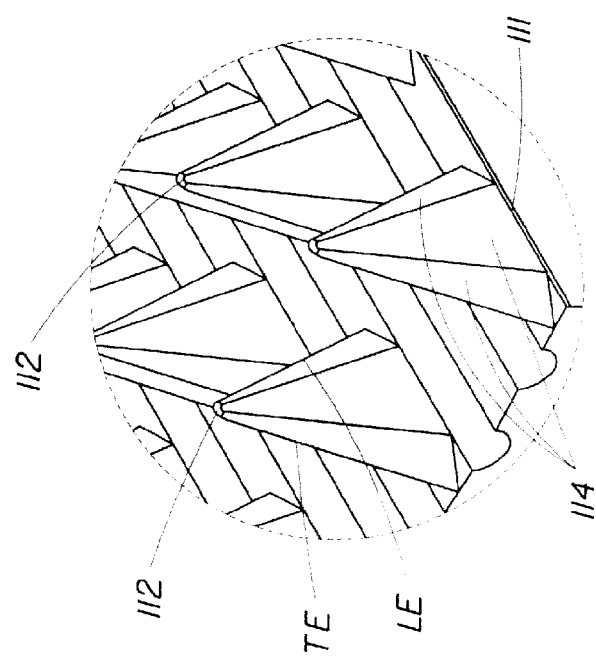
FIG. 10 is a magnified perspective view of a portion of the apparatus shown in FIG. 9.

FIG. 9 shows a portion of one embodiment of a roller 104 having a plurality of teeth 110 useful for making an apertured web 1. An enlarged view of the teeth 110 shown in FIG. 9 is shown in FIG. 10. As shown in FIG. 10, each tooth 110 has a base 111, a tooth tip 112, a leading edge LE and a trailing edge TE. The tooth tip 112 can be generally pointed, blunt pointed, or otherwise shaped so as to stretch and/or puncture the precursor web 20. Teeth 110 can have generally flattened, blade-like shape. That is, as opposed to round, pin-like shapes that are generally round in cross section, teeth 110 can be elongated in one dimension, having generally non-round, elongated cross-sectional configurations. For example, at their base, teeth 110 can have a tooth length TL and a tooth width TW exhibiting a tooth aspect ratio AR of TL/TW of at least 2, or at least about 3, or at least about 5, or at least about 7, or at least about 10 or greater. In one embodiment, the aspect ratio AR of cross-sectional dimensions remains substantially constant with tooth height.

In one embodiment of roller 104, teeth 110 can have a uniform circumferential length dimension TL of about 1.25 mm measured generally from the leading edge LE to the trailing edge TE at the base 111 of the tooth 110, and a tooth width TW of about 0.3 mm measured generally perpendicularly to the circumferential length dimension at the base. Teeth can be uniformly spaced from one another circumferentially by a distance TD of about 1.5 mm. For making a soft, fibrous three-dimensional apertured web 1 from a precursor web 20 having a basis weight in the range of from about 5 gsm to about 200 gsm, teeth 110 of roll 104 can have a length TL ranging from about 0.5 mm to about 3 mm, a tooth width TW of from about 0.3 mm to about 1 mm, and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum approaching the tooth height TH).

Of course, E, P, TH, TD and TL can each be varied independently of each other to achieve a desired size, spacing, and area density of apertures 6 (number of aperture 6 per unit area of apertured web 1). For example, to make apertured films and nonwovens suitable for use in sanitary napkins and other absorbent articles, tooth length TL at the base can range between about 2.032 mm to about 3.81 mm; tooth width TW can range from about 0.508 mm to about 1.27 mm; tooth spacing TD can range from about 1.0 mm to about 1.94 mm; pitch P can range from about 1.106 mm to about 2.54 mm; and tooth height TH can be from about 2.032 mm to about 6.858 mm. Depth of engagement E can be from about 0.5 mm to about 5 mm. The radius of curvature R of the tooth tip 112 can be from 0.001 mm to about 0.009 mm. Without being bound by theory, it is believed that tooth length TL at the base can range between about 0.254 mm to about 12.7 mm; tooth width TW can range from about 0.254 mm to about 5.08 mm; tooth spacing TD can range from about 0.0 mm to about 25.4 mm (or more); pitch P can range from about 1.106 mm to about 7.62 mm; tooth height TH can range from 0.254 mm to about 18 mm; and depth of engagement E can range from 0.254 mm to about 6.35 mm. For each of the ranges disclosed, it is disclosed herein that the dimensions can vary within the range in increments of 0.001 mm from the minimum dimension to the maximum dimension, such that the present disclosure is teaching the range limits and every dimension in between in 0.001 mm increments (except for radius of curvature R, in which increments are disclosed as varying in 0.0001 mm increments).

Without wishing to be bound by theory, and consistent with currently-pending tool designs, it is believed that other dimensions are possible for use in the method and apparatus of the present invention. For example, tooth length TL at the base can range can be from about 0.254 mm to about 12.7 mm, and can include 4.42 mm, 4.572 mm and about 5.56 mm; tooth width TW can range from about 0.254 mm to about 5.08 mm, and can include 1.78 mm; tooth spacing TD can range from about 0.0 mm to about 25.4 mm, and can include 2.032 mm; pitch P can range from about 1.106 mm to about 7.62 mm; tooth height TH can range from 0.254 mm to about 18 mm, and can include 5.08 mm; and depth of engagement E can range from 0.254 mm to about 6.35 mm. Radius of curvature can range from about 0.00 mm to about 6.35 mm. For each of the ranges disclosed, it is disclosed herein that the dimensions can vary within the range in increments of 0.001 mm from the minimum dimension to the maximum dimension, such that the present disclosure is teaching the range limits and every dimension in between in 0.001 mm increments (except for radius of curvature R, in which increments are disclosed as varying in 0.0001 mm increments).

Figure 11:
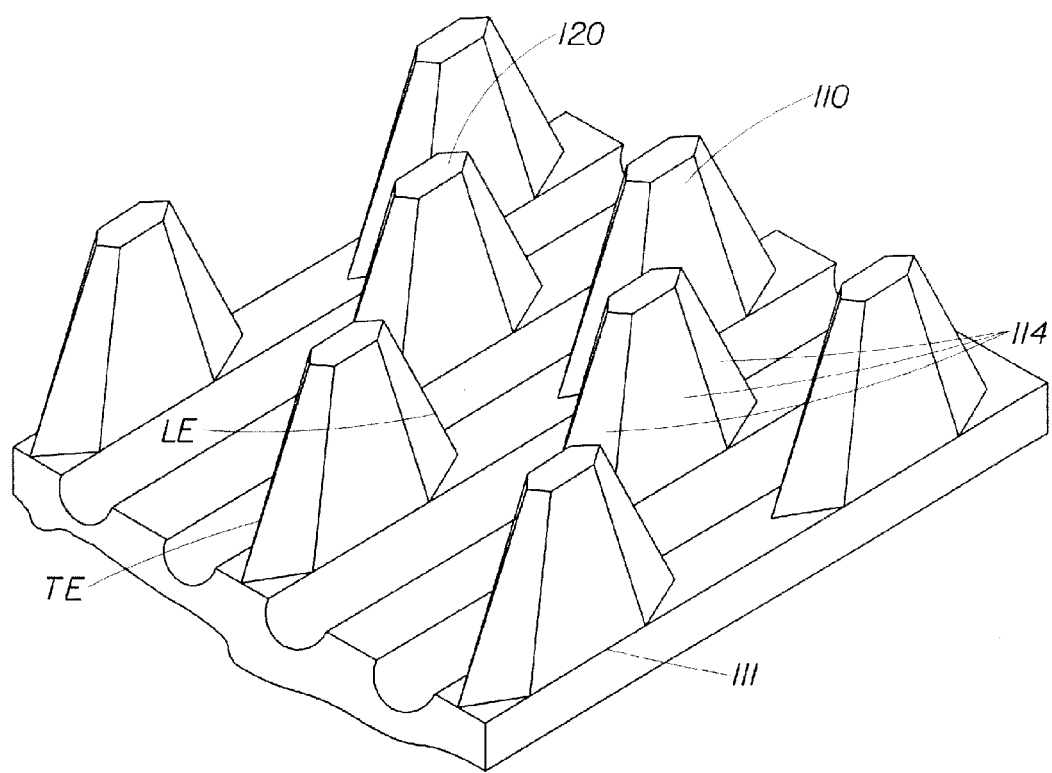
FIG. 11 is a perspective view of an alternative configuration for teeth on the apparatus shown in FIG. 2.

In one embodiment, to make the volcano-shaped structures 8 and/or apertures 6 of apertured web 1, the LE and TE should taper to a point in a generally pyramidal or frustro-conical shape which can be described as being shaped like a shark's tooth. As shown in FIG. 10, the generally pointed pyramidal shark tooth shape can have six sides 114, each side being generally triangular in shape. The vertex of two sides makes up the leading edge LE and the vertex of two sides makes up the trailing edge TE of tooth 110. The vertices of the leading or trailing edge can be relatively sharp, or can be machined to have a rounded radius of curvature. The radius of curvature of the tooth tip can be 0.005 m Other tooth shapes can be utilized to make apertures. As shown in FIG. 11, for example, the generally pyramidal shapes shown in FIG. 9 can be truncated so as to remove the pointedness of tips 112. Truncation can be made at a predetermined distance from base 111 such that a generally flattened region 120 is produced at the distal end of tooth 110. Generally flattened region 120 can have an area shape corresponding to the cross-sectional shape of tooth 110. Thus, generally flattened region 120 can also be elongated, that is, having a length dimension greater than a width dimension and an aspect ratio AR corresponding to the aspect ratio of tooth 110. In one embodiment, flattened region 120 can transition to sides 114 at generally sharp vertices, or the transition can be at a radius of curvature, providing for a smooth, rounded, flattened tooth tip.

Figure 12:
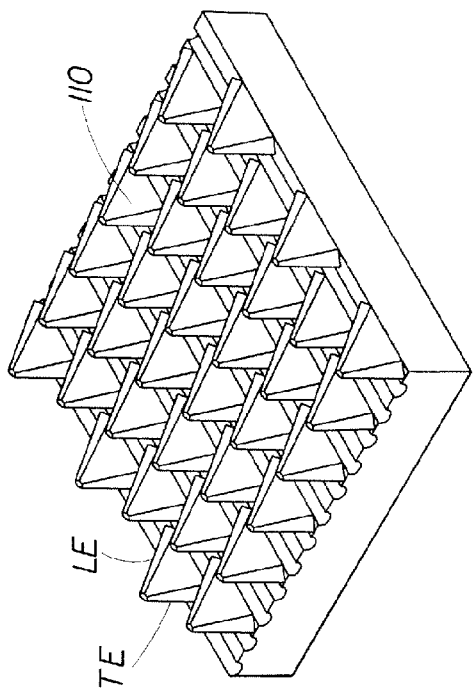
FIG. 12 is a perspective view of a portion of the apparatus shown in FIG. 2.

In another embodiment, as shown in FIG. 12, teeth 110 can have at least one edge that extends generally perpendicularly with respect to the surface of roller 104. As shown in the partial perspective view of roller 104 in FIG. 12, for example, teeth resembling shark fins can have a leading edge LE that angles toward tip tooth 112, and a trailing edge TL that extends generally perpendicular from base 111 toward tip tooth 112. In another embodiment, the tooth 110 can have the same shape, but the leading and trailing edges reversed such that the generally perpendicular edge is the leading edge.

Figure 13:
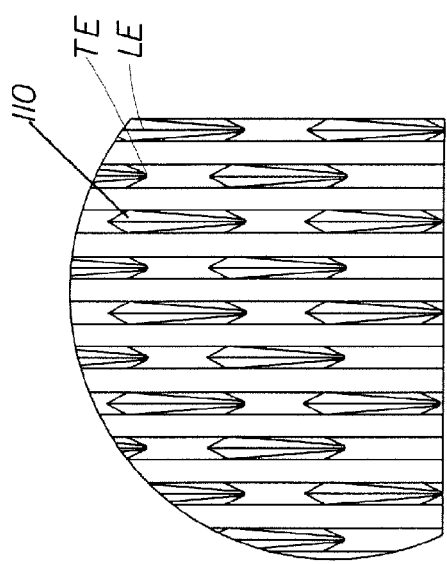
FIG. 13 is a top view of the portion of the apparatus shown in FIG. 12.
Figure 14:
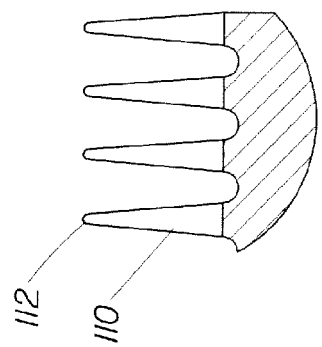
FIG. 14 is a plan view of a portion of the apparatus shown in FIG. 12.

FIG. 13 is a top view of the portion of roller 104 shown in FIG. 12. Various dimensions are shown in the illustrated embodiment, including the angles produced by the sides 114 making up the leading and trailing edges. Likewise, FIG. 14 is a detail of the teeth shown in FIG. 12 showing representative dimensions. In general, while the dimensions shown are those currently believed to be beneficial for making three-dimensional formed films useful as topsheets on disposable absorbent articles, all dimensions can be varied as necessary depending on the desired aperture density, spacing, size, and the web type of precursor web 20.

Figure 15:
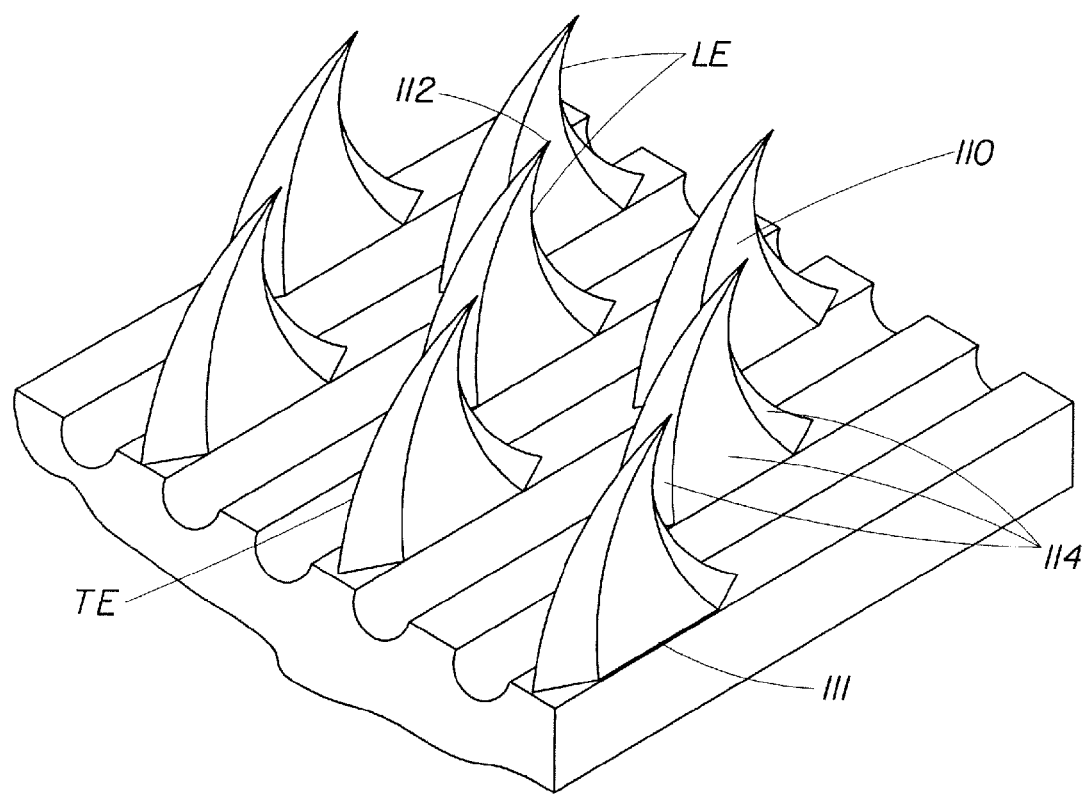
FIG. 15 is a perspective view of an alternative configuration for teeth on the apparatus shown in FIG. 2.

In another embodiment, as shown in the partial perspective view of roller 104 in FIG. 15, teeth 110 can have a degree of curvature, at least along one or both of the LE and/or TE. Curved teeth 110 can be shaped generally like a bear claw, having a sharp point, a rounded point, or a flattened point. The curvature of the curved tooth can be oriented to be curving in the direction of rotation, or in the other direction, or the orientation may be mixed on roll 104.

Without being bound by theory, it is believed that having relatively sharp tips on teeth 110 permits the teeth 110 to punch through precursor web 20 "cleanly", that is, locally and distinctly, so that the resulting web 1 can be described as being predominantly "apertured" rather than predominantly "embossed". In one embodiment, puncture of precursor web 20 is clean with little deformation of web 20, such that the resulting web is a substantially two-dimensional perforated web.

It is also contemplated that the size, shape, orientation and spacing of the teeth 110 can be varied about the circumference and width of roll 104 to provide for varied apertured web 1 properties and characteristics.

Additionally, substances such as lotions, ink, surfactants, and the like can be sprayed, coated, slot coated, extruded, or otherwise applied to apertured web 1 or before or after entering nip 116. Any processes known in the art for such application of treatments can be utilized.

After apertured web 1 is formed, it can be taken up on a supply roll 160 for storage and further processing as a component in other products. Or apertured web 1 can be guided directly to further post processing, including incorporation into a finished product, such as a disposable absorbent product.

Although apertured web 1 is disclosed in the illustrated embodiments as a single layer web made from a single layer precursor web 20, it is not necessary that it be so. For example, a laminate or composite precursor web 20 having two or more layers or plies can be used. In general, the above description for apertured web 1 holds, recognizing that a web 1 formed from a laminate precursor web could be comprised of volcano like structures 8 wherein the sidewalls 9 comprise one or more of the precursor web materials. For example, if one of the materials of a composite precursor web has very low extensibility, teeth 110 may punch more or less cleanly through, such that it does not contribute material to the volcano like structure sidewalls 9. Therefore, a three-dimensional web made from a composite or laminate precursor web 20 may comprise volcano like side walls 9 on apertures 6 that comprise material from less than all the precursor web materials.

Figure 16A:
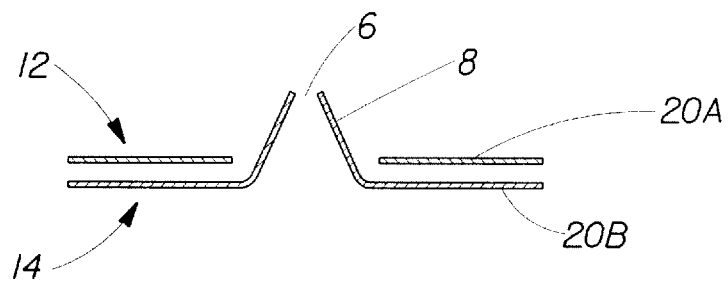
FIGS. 16A-16C are schematic representations of various alternative laminate web configurations.
Figure 16B:
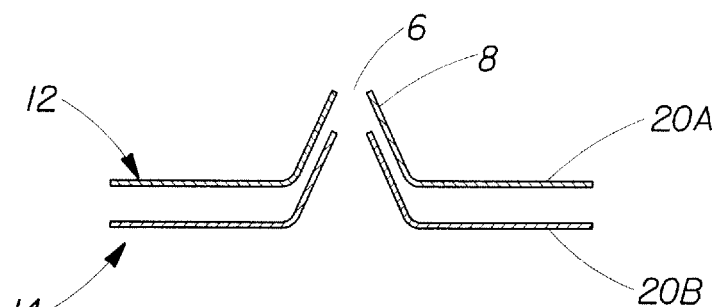
Figure 16C:
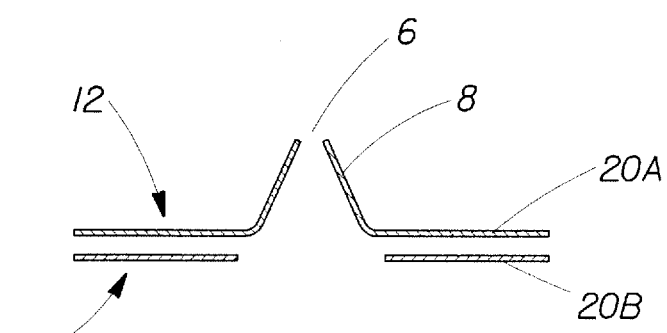

FIGS. 16A-16C show schematically various configurations of two layer composite webs 1 having a first surface 12 and a second surface 14, wherein extending from the second surface 12 are volcano-shaped structures 8. In general, two precursor webs designated as 20A and 20B can each be either a polymer film or a nonwoven web and processed together in layered relationship by the apparatus 150 or 200 as described above. Depending on the properties of each, such as ductility and extensibility, the result can be that either of precursor webs 20A or 20B can extend to form a three-dimensional volcano-like structure 8 as shown in FIGS. 16A and 16C. The other of precursor web 20A or 20B can simply be punched through to form a two-dimensional aperture, thereby not forming any substantially three-dimensional structure. However, as shown in FIG. 16B, both of precursor webs 20A or 20B can extend out of plane to form a three-dimensional volcano-like structure 8.

Multilayer apertured webs 1 made from composite laminate precursor webs 20 can have significant advantages over single layer apertured webs 1. For example, an aperture 6 from a multilayer web 1 using two precursor webs, 20A and 20B, can comprise fibers (in the case of nonwoven webs) or stretched film (in the case of film webs) in a "nested" relationship that "locks" the two precursor webs together. One advantage of the locking configuration is that, while adhesives or thermal bonding may be present, the nesting allows forming a laminate web without the use or need of adhesives or additional thermal bonding between the layers. In other embodiments, multilayer webs can be chosen such that the fibers in a nonwoven web layer have greater extensibility than an adjacent film layer. Such webs can produce apertures 6 by pushing fibers from a nonwoven layer up and through an upper film layer which contributes little or no material to volcano-shaped structure 8 sidewalls 9.

In a multilayer apertured web 1 each precursor web can have different material properties, thereby providing apertured web 1 with beneficial properties. For example, apertured web 1 comprising two (or more) precursor webs, e.g., first and second precursor webs 20A and 20B can have beneficial fluid handling properties for use as a topsheet on a disposable absorbent article. For superior fluid handling on a disposable absorbent article, for example, second precursor web 20B can form an upper film layer (i.e., a body-contacting surface when used as a topsheet on a disposable absorbent article) and be comprised of relatively hydrophobic polymer. First precursor web 20A can be a nonwoven fibrous web and form a lower layer (i.e., disposed between the topsheet and an absorbent core when used on a disposable absorbent article) comprised of relatively hydrophilic fibers. Fluid deposited upon the upper, relatively hydrophobic layer can be quickly transported to the lower, relatively hydrophilic, layer. For some applications of disposable absorbent articles, the relative hydrophobicity of the layers could be reversed, or otherwise modified. In general, the material properties of the various layers of web 1 can be changed or modified by means known in the art for optimizing the fluid handling properties of web 1.

A distinct benefit of the apparatus 150 or 200 as described above for forming apertured webs for use in disposable absorbent articles is the ability to adapt and position the apparatus 150 or 200 as a unit operation in an existing process for making such articles. For example, apertured web 1 can be a topsheet in an absorbent article such as a sanitary napkin. Rather than make the apertured web off line, perhaps at a geographically remote location, apertured web 1 can be made on line by putting forming apparatus 150 in line with the supply of topsheet material on a production line for making sanitary napkins. Doing so provides several distinct advantages. First, having forming apparatus 150 making apertures in the topsheet directly on the sanitary napkin production line eliminates the need to purchase apertured webs, which can be costly when made by traditional processes, such as vacuum forming, or hydroforming. Second, forming apertures on the sanitary napkin production line minimizes the amount of compression and flattening that three-dimensional volcano-shaped regions are subject to. For example, when three-dimensional apertured formed film webs are produced and shipped on rolls, a significant amount of compression, as well as permanent compression set, of the formed film apertures takes place. Such compression is detrimental to the operation of the web as a fluid pervious topsheet. Third, toothed roll 104 can be configured such that toothed regions are made in predetermined patterns, so that the apertured portion of an apertured topsheet is formed in a predetermined pattern. For example, a topsheet can be make on line in which the apertures are only disposed in the middle portion of a sanitary napkin. Likewise, apertures can be formed such that apertured regions are registered with other visible components, including channels, indicia, color signals, and the like.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for aperturing a web, said apparatus comprising two intermeshing counter-rotating rolls that form a nip therebetween, said apparatus comprising:
   a) a generally cylindrical first roll, said first roll having a surface, a circumference, and a first axis, said first roll comprising a plurality of circumferentially extending ridges and grooves on the surface of the first roll that are oriented perpendicular to said first axis, wherein said ridges have a top surface and said grooves have a bottom surface; and
   b) a generally cylindrical second roll, said second roll having a surface, a circumference, and a second axis extending in a direction that is parallel to said first axis, said second roll comprising:
      a plurality of circumferentially extending ridges and grooves on the surface of the second roll that are oriented perpendicular to said second axis, wherein said ridges have a top surface and said grooves have a bottom surface; and
      a plurality of spaced apart teeth extending outwardly from the top surface of said ridges on said second roll, said teeth having a base and a single tip, wherein the top surface of the ridges on said second roll are disposed between the tips of said teeth and the bottom surface of said grooves on said second roll in a direction radially outward from the surface of said second roll, wherein when looking in the direction of the second axis, the teeth are tapered from the base to the tip, and wherein the base of said teeth have a cross-sectional length dimension greater than a cross-sectional width dimension.

2. The apparatus of claim 1 wherein the ridges and grooves on the first roll extend unbroken about the entire circumference of the first roll.

3. The apparatus of claim 1 wherein the ridges on the first roll have breaks therein.

4. The apparatus of claim 1 wherein the teeth on the second roll are arranged in circumferentially extending rows comprising at least a first row of teeth and an adjacent row of teeth separated by a groove therebetween, and the spaced apart teeth in the first row are staggered relative to the teeth in the adjacent row wherein the teeth in the adjacent row at least partially align with the spaces between the teeth in the first row when viewed looking in the direction of the axis of the second roll.

5. The apparatus of claim 1 wherein the ridges of the first roll extend into the grooves of the second roll, and the teeth of the second roll extend into the grooves of the first roll.

6. An apparatus for aperturing a web, said apparatus comprising two intermeshing counter-rotating rolls that form a nip therebetween, said apparatus comprising:
   a) a generally cylindrical first roll, said first roll having a surface, a circumference, and a first axis, said first roll comprising a plurality of circumferentially extending ridges and grooves on the surface of the first roll that are oriented perpendicular to said first axis, wherein said ridges have a top surface and said grooves have a bottom surface; and a plurality of spaced apart teeth extending outwardly from the surface of the first roll; and
   b) a generally cylindrical second roll, said second roll having a surface, a circumference, and a second axis extending in a direction that is parallel to said first axis, said second roll comprising:
      a plurality of circumferentially extending ridges and grooves on the surface of the second roll that are oriented perpendicular to said second axis, wherein said ridges have a top surface and said grooves have a bottom surface; and
      a plurality of spaced apart teeth extending outwardly from the top surface of said ridges on said second roll, said teeth having a base and a single tip, wherein the top surface of the ridges on said second roll are disposed between the tips of said teeth and the bottom surface of said grooves on said second roll in a direction radially outward from the surface of said second roll, wherein when looking in the direction of the second axis, the teeth are tapered from the base to the tip, and wherein the base of said teeth have a cross-sectional length dimension greater than a cross-sectional width dimension.

7. The apparatus of claim 6 wherein said teeth on said first roll have a base and a tip, wherein the base of the teeth on said first roll have a cross-sectional length dimension greater than a cross-sectional width dimension.

8. The apparatus of claim 6 wherein the spaced apart teeth on said first roll extend outwardly from the top surface of said ridges on said first roll, and said teeth have a base and a tip, wherein the top surface of the ridges on said first roll are disposed between the tips of said teeth and the bottom surface of said grooves on said first roll in a direction radially outward from the surface of said first roll.

9. A method for making apertures in a web, said method comprising:
   a) providing a precursor web material;
   b) providing an apparatus comprising a pair of counter-rotating, intermeshing rolls that form a nip therebetween, said rolls comprising:
      1) a generally cylindrical first roll, said first roll having a surface, a circumference, and a first axis, said first roll comprising a plurality of circumferentially extending ridges and grooves on the surface of the first roll that are oriented perpendicular to said first axis, wherein said ridges have a top surface and said grooves have a bottom surface; and
      2) a generally cylindrical second roll, said second roll having a surface, a circumference, and a second axis that is parallel to said first axis, said second roll comprising:
         a plurality of circumferentially extending ridges and grooves on the surface of the second roll that are oriented perpendicular to said second axis, wherein said ridges have a top surface and said grooves have a bottom surface; and
         a plurality of spaced apart teeth extending outwardly from the top surface of said ridges on said second roll, said teeth having a base and a single tip, wherein the top surface of the ridges on said second roll are disposed between the tips of said teeth and the bottom surface of said grooves on said second roll in a direction radially outward from the surface of said second roll, wherein when looking in the direction of the second axis, the teeth are tapered from the base to the tip, and wherein the base of said teeth have a cross-sectional length dimension greater than a cross-sectional width dimension; and
   c) moving said precursor web through the nip of said counter-rotating, intermeshing rolls to form apertures in said precursor web as the teeth on said second roll intermesh with grooves on the first roll to form an apertured web.

10. The method of claim 9 wherein said web has two sides, and the method forms three dimensional portions in the web surrounding said apertures that extend outwardly from one side of the web.

11. The method of claim 9 wherein said precursor web comprises a film that is pre-textured with microscopic aberrations.

12. The method of claim 11 wherein the aberrations are selected from the group consisting of: bumps, embossments, holes, non-apertured protrusions, and fibrils.

13. The method of claim 9 wherein said counter-rotating, intermeshing rolls comprise a unit operation on a disposable absorbent article production line.

14. The method of claim 9 wherein the first roll further comprises a plurality of spaced apart teeth extending outwardly from the surface of said first roll.

15. The method of claim 14 wherein said teeth on said first roll have a base and a tip, wherein the base of the teeth on said first roll have a cross-sectional length dimension greater than a cross-sectional width dimension.

16. The method of claim 14 wherein the spaced apart teeth on said first roll extend outwardly from the top surface of said ridges on said first roll, and said teeth have a base and a tip, wherein the top surface of the ridges on said first roll are disposed between the tips of said teeth and the bottom surface of said grooves on said first roll in a direction radially outward from the surface of said first roll.

17. The method of claim 16 wherein the teeth on said first roll intermesh with the grooves on said second roll to form a first set of apertures in said precursor web, and the teeth on said second roll intermesh with the grooves on the first roll to form a second set of apertures in said web.

18. The method of claim 16 wherein the teeth on the first roll and the teeth on the second roll are arranged in the form of a pattern, and the pattern of teeth on the first roll and the pattern of teeth on the second roll are the same.

19. The method of claim 16 wherein the teeth on the first roll and the teeth on the second roll are arranged in the form of a pattern, and the pattern of teeth on the first roll and the pattern of teeth on the second roll are different.

20. The method of claim 16 wherein the teeth on the first roll and the teeth on the second roll are arranged in the form of a pattern, and the pattern of teeth on the first roll and the pattern of teeth on the second roll are located in the same regions of the corresponding rolls.

21. The method of claim 16 wherein the teeth on the first roll and the teeth on the second roll are arranged in the form of a pattern, and the pattern of teeth on the first roll and the pattern of teeth on the second roll are located in the different regions of the corresponding rolls.

22. The method of claim 16 wherein said precursor web has two sides, and after said method said apertured web has three dimensional portions surrounding the apertures in said first set of apertures that extend outwardly from one side of the web, and three dimensional portions surrounding the apertures in said second set of apertures that extend outwardly from the other side of the web.

23. The method of claim 16 wherein the teeth on one of said rolls form said apertures into said web, and the teeth on the other roll form aberrations, micro-apertures, or micro-patterns into the web.

24. The apparatus of claim 1 wherein the teeth on said second roll have a configuration selected from one of the following configurations: generally pyramidal; frusto-conical; shark tooth shaped; shark fin shaped; and bear claw shaped.

25. The apparatus of claim 1 wherein the teeth on said second roll are pointed.

26. The apparatus of claim 1 wherein the teeth on said second roll are blunt pointed.

27. The apparatus of claim 1 wherein the teeth on said second roll are truncated.

* * * * *